United States Patent
Wang et al.

(10) Patent No.: US 10,821,137 B2
(45) Date of Patent: Nov. 3, 2020

(54) PHARMACEUTICAL COMPOSITION FOR PROMPTING THE SKIN WOUND HEALING AND METHOD FOR PRODUCTION

(71) Applicant: TEKHO MARINE BIOTECH CO., LTD., Tainan (TW)

(72) Inventors: Tai-Lai Wang, Tainan (TW); Chih-Mou Wu, Tainan (TW)

(73) Assignee: Tekho Marine Biotech Co., Ltd., Tainan (TW)

( * ) Notice: Subject to any disclaimer, the term of this patent is extended or adjusted under 35 U.S.C. 154(b) by 0 days.

(21) Appl. No.: 16/434,364

(22) Filed: Jun. 7, 2019

(65) Prior Publication Data

US 2020/0268808 A1    Aug. 27, 2020

(30) Foreign Application Priority Data

Feb. 27, 2019  (TW) .............................. 108106784 A

(51) Int. Cl.
| | |
|---|---|
| *A61K 35/60* | (2006.01) |
| *A61Q 19/00* | (2006.01) |
| *A61P 17/02* | (2006.01) |
| *A61K 8/98* | (2006.01) |

(52) U.S. Cl.
CPC .............. *A61K 35/60* (2013.01); *A61K 8/987* (2013.01); *A61P 17/02* (2018.01); *A61Q 19/00* (2013.01)

(58) Field of Classification Search
CPC ....................................................... A61K 35/60
See application file for complete search history.

(56) References Cited

U.S. PATENT DOCUMENTS

2012/0107412 A1*  5/2012  Gammelsaeter ....... A61K 8/676
                                                                 424/582

* cited by examiner

*Primary Examiner* — Qiuwen Mi
(74) *Attorney, Agent, or Firm* — Rosenberg, Klein & Lee

(57) ABSTRACT

A composition for use in wound healing and therefor is disclosed. The multiple components of fish fertilized roe are extracted. By virtue of its ability as an anti-oxidant to eliminate free radicals, inhibition of tyrosinase activity and facilitate the mass secretion of collagen from skin fibroblasts in order to promote skin whitening, anti-aging and wound healing. Accordingly, skin all-round repair is achieved, which is used as a cosmetic raw material and a wound dressing.

11 Claims, 5 Drawing Sheets

PHARMACEUTICAL COMPOSITION FOR PROMPTING THE SKIN WOUND HEALING AND METHOD FOR PRODUCTION

TECHNICAL FIELD

The instant disclosure relates to a composition which can be used in wound-healing, in particular, the use of fertilized roe extract which has antioxidant activity, inhibition of melanin production, as well as facilitating collagen synthesis and cell proliferation to promote wound healing, and to reduce the time and possibility for wounds to be infected by environmental pathogens.

BACKGROUND OF RELATED ARTS

According to physiological definition, the process of wound healing is divided into three phases: inflammation, proliferation, and maturation, in which if the inflammatory period becomes longer, it will increase the chance of infection and delay of wound healing. Furthermore, the wound healing is divided into the repairs of epidermal proliferation and dermal proliferation. Generally, the epidermis is healed faster, while the dermis takes a long time to complete the tissue remodeling and return to the original state.

Asian aquaculture have made considerable progress, and the technology of breeding domesticated wild fish species for use of breeding fish is globally leading. However, the number of fertilized roes produced during the breeding season of the fish is hatched and stocked in accordance with the market demand. Therefore, when the wind direction of the off-season or the stocking variety changes, the phenomenon of excessive fertilized roes of the variety will be caused, and it is a pity that it can only be discarded. Because the fertilized roes have the ability to develop into a complete individual, it also represents that the fertilized roes are rich in all kinds of factors that may be closely related to cell proliferation and differentiation, such as growth factors, cytokines, and the like. If the fertilized roes can be further extracted and utilized, it is expected to be applied to wound care, which not only makes the best use of it, but also enhances the added value of the aquaculture.

SUMMARY

Accordingly, for promoting the healing of skin wounds and increasing additional value of aquaculture. A pharmaceutical composition for prompting the skin wound healing, which includes a fertilized roe extract of a fish, is proposed. The fertilized roe extract is obtained by extracting a fertilized roe by using low-temperature water.

Further, the fish is a fish of any genus of *Perciformes*.

Further, the fish includes a fish of any genus of Epinephelinae subfamily of Serranidae family.

Further, the fish is selected from the group consisting of *Epinephelus lanceolatus, Epinephelus fuscoguttatus, Epinephelus fuscoguttatus* ♀x *Epinephelus lanceolatus* ♂, *Epinephelus coioides, Epinephelus malabaricus, Cromileptes altivelis, Plectropomus leopardus, Epinephelus akaara, Epinephelus bruneus, Epinephelus septemfasciatus* or a combination thereof.

Further, the skin wound is selected from the group consisting of an incised injury, a bruise, a burn, a scald, a sunburn, or a combination thereof.

Further, the fertilized roe extract has a concentration of generally from 0.01 to 1 wt %.

Further, the pharmaceutical composition for prompting the skin wound healing further includes one or more pharmaceutically acceptable carriers Further, the fertilized roe extract is in the form of a liquid, a powder, a granule, a gel, a cream or a dressing.

Further, the pharmaceutical composition for prompting the skin wound healing includes an oral or topical dosage form.

A use of a fertilized roe extract for the preparation of a medicament for prompting skin wound healing is further proposed.

A collagen synthesis promoter, which includes the fertilized roe extract, is further proposed.

A pharmaceutical cosmetic product is further proposed, which includes applying the aforementioned pharmaceutical composition for prompting the skin wound healing, and having the effects of accelerating repair of skin damage, inhibiting tyrosinase activity and facilitating collagen synthesis.

A fertilized roe extract used for preparing a cosmetic raw material for inhibiting tyrosinase activity and facilitating collagen synthesis is further proposed.

A wound dressing for promoting skin wound healing is further proposed, which includes applying the aforementioned pharmaceutical composition for promoting skin wound healing for covering to a wound.

A fertilized roe extract used for preparing a wound dressing for promoting skin wound healing is further proposed.

An anti-oxidant which includes and uses the fertilized roe extract is further proposed. The fertilized roe extract has the ability to scavenge 50% of free radicals whiles its concentration is 0.21 wt %.

According to the above technical features, the following effects can be achieved:

1. By extracting fertilized roe extracts for use in a skin wound to promote wound healing and significantly shorten the inflammatory period. If the wound damaged the dermis, it can also reconstruct the papillary layer of the dermis, making the wound on epidermis and dermis better.

2. By experiments it is verified that the fertilized roe extracts have the antioxidant activity of eliminating free radicals, inhibit the activity of tyrosinase and facilitate the mass secretion of collagen from skin fibroblasts, so it can be further applied to wound dressings of medical equipment and cosmetic products, so as to not only achieve whitening and anti-aging effects, but also accelerate the healing of skin wounds (such as skin laser minimally invasive, burns, scalds, incised injuries, bruises or sunburns), making it widely applicable.

DETAILED DESCRIPTIONS OF EMBODIMENTS

Figure 1:
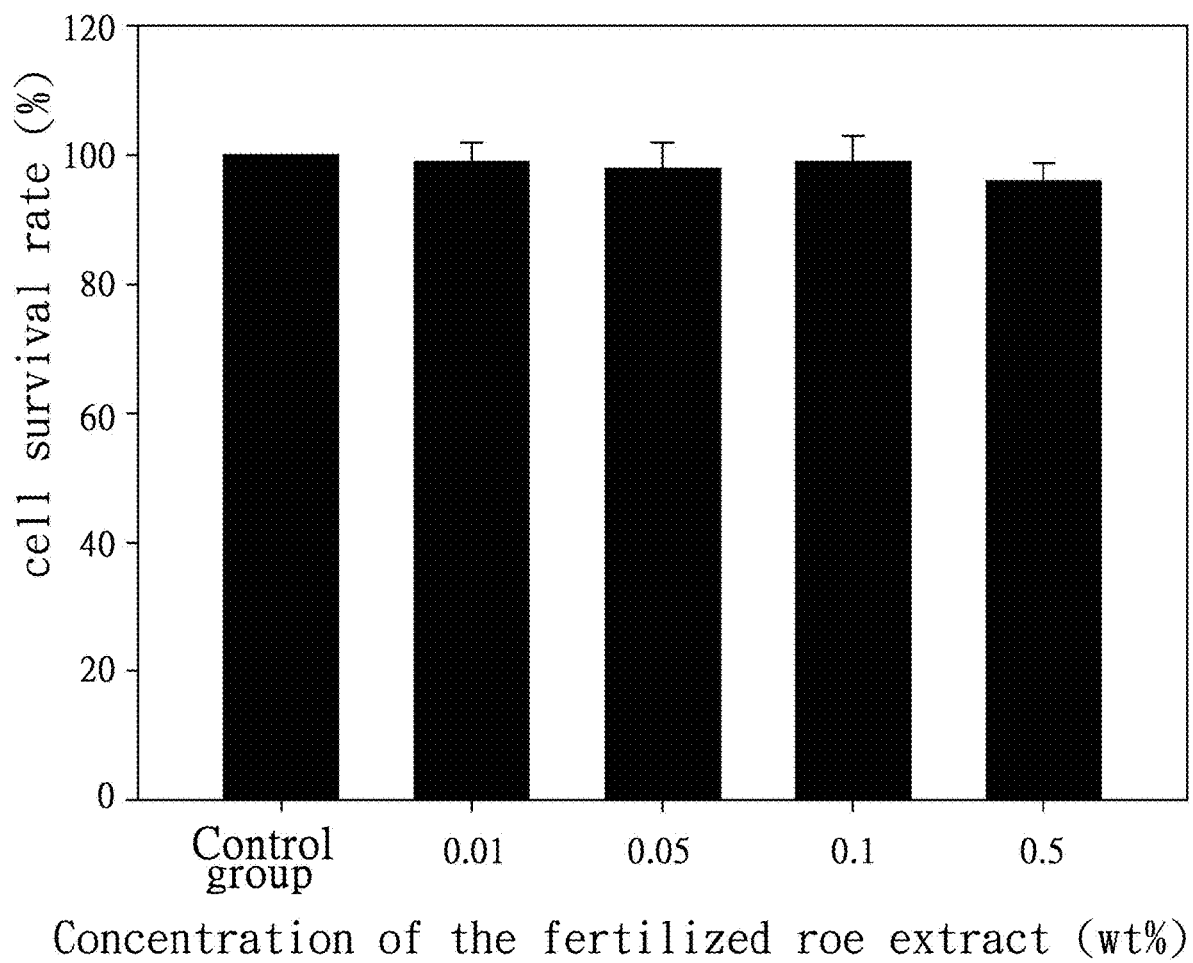
FIG. 1 is a graph showing the survival rate in the cytotoxicity test of the fertilized roe extract according to one embodiment of the present invention.

In combination with the above technical features, the main effects of the pharmaceutical composition of the present disclosure for promoting the skin wound healing will be clearly shown in the following examples.

First, a pharmaceutical composition for prompting the skin wound healing, which contains a fertilized roe extract of a fish. The fertilized roe extract is obtained by a conventional low-temperature water extraction method, including steps of homogenizing a fertilized roe at a low temperature (10 to 18° C.) using an ultrasonic or high-speed homogenizer, making the protein or peptide molecules in the fertilized roe released into the aqueous solution and then subjected to multi-stage impurity filtration (1 mm to 0.1 μm in pore size filter/membrane) and deodorization process (1 g activated carbon/1 L extract).

It is understood by those of ordinary skill in the art that the fertilized roe extract is a concept of protein summation, meaning that all proteins and peptide molecules related to cell proliferation and differentiation in the fertilized roe are retained since it may contain many unknown growth factors or cytokines. However, before the global genomic database has not yet completed the sequencing of the genus of Epinephelinae subfamily of Serranidae family, it is still impossible to separate and define the unknown growth factors or cytokines (still no standard available). Only the fertilized roe extract can be defined by the concept of protein summation, and the protein and peptide molecules which are most beneficial to cell proliferation and differentiation can be retained as much as possible, so as to be applied to anti-aging cosmetic products and pharmaceutical products.

Preferably, the fish is a fish of any genus of *Perciformes*. Preferably, the fish may be a fish of any genus of Epinephelinae subfamily of Serranidae family. Preferably, the fish is selected from the group consisting of: *Epinephelus lanceolatus, Epinephelus fuscoguttatus, Epinephelus fuscoguttatus* ♀ x *Epinephelus lanceolatus* ♂*, Epinephelus coioides, Epinephelus malabaricus, Cromileptes altivelis, Plectropomus leopardus, Epinephelus akaara, Epinephelus bruneus*. In addition, the fertilized roe can also be a new variety of fertilized roe produced by the any two of the above-mentioned varieties, and may have excellent inheritance of the parent varieties. The fish refers to the fish species that can be used for large-scale artificial breeding after being domesticated. Because of the large number of breeding, the number of fertilized roes can be quantified and produce extracts to meet the market demand. The value for industrial use of the fertilized roe extracts is substantial.

In one embodiment of the present invention, the fertilized roe extracts obtained by extracting the fertilized roe mixtures with equal proportion mixing from several varieties of fish such as *Epinephelus lanceolatus, Epinephelus fuscoguttatus, Epinephelus fuscoguttatus* ♀ x *Epinephelus lanceolatus* ♂*, Epinephelus coioides, Epinephelus malabaricus* are used as an illustrative example, but not limited the fertilized roe as a multi-variety mixture, that is a single variety of fertilized roe is also acceptable. Those of ordinary skill in the related art can understand that the extracts obtained from the fertilized roes of the same species of fish have effects within a presumed range and can be regarded as the same or similar.

In one embodiment of the present invention, the fertilized roe extract has a concentration of generally from 0.01 to 1 wt %. Regarding the definition of the concentration range, theoretically, the higher the concentration is, the better the effect should be; however the skin safety should still be considered. Therefore, after the skin patch safety evaluation, the concentration is 1 wt % as the upper limit. Preferably, the fertilized roe extract is in the form of a liquid or gel, or freeze-dried into a powder or granules; or emulsified into a cream, thereby meeting the requirements of different dosage forms. Certainly, the pharmaceutical composition according to one embodiment of the present invention for prompting skin wound healing may further contain one or more pharmaceutically acceptable carriers to make the dosage form more diversified. Preferably, the pharmaceutical composition includes an oral or topical dosage form, and since the fertilized roes of the traditional edible fish is also recognized as an edible food, it can also be used as an oral dosage form such as use for the oral intima. In one embodiment of the present invention, a topical dosage form as liquid-like (a conventional essence dosage form) is used as an example for performing various tests.

According to the present disclosure, a use of a fertilized roe extract for the preparation of a medicament for prompting skin wound healing is provided.

According to the present disclosure, a pharmaceutical cosmetic product is provided. The pharmaceutical cosmetic product includes the pharmaceutical composition for prompting the skin wound healing, bringing about the effects of accelerating repair of skin damage, inhibiting tyrosinase activity and facilitating collagen synthesis.

According to the present disclosure, a fertilized roe extract used for preparing a cosmetic raw material for inhibiting tyrosinase activity and facilitating collagen synthesis is provided.

According to the present disclosure, a wound dressing for promoting skin wound healing is provided, which includes applying the pharmaceutical composition for promoting healing a skin wound for covering to a wound.

According to the present disclosure, a fertilized roe extract used for preparing a wound dressing for promoting healing a skin wound is provided, According to the present disclosure, an anti-oxidant which includes and uses the fertilized roe extract is further proposed. The fertilized roe extract has the ability to scavenge 50% of free radicals whiles its concentration is 0.21 wt %.

The embodiments of the present invention are described as follows:

1. Cytotoxicity Tests

With refer to FIG. 1, it is a graph showing the survival rate in the cytotoxicity test of the fertilized roe extract according to one embodiment of the present invention. The cell viability assay (MTT assay), which can be understood by those of ordinary skill in the art, to analyze the effects of the fertilized roe extract on the growth of human skin fibroblasts (Hs68), which is administered at different concentrations of the fertilized roe extracts (0.01 wt %, 0.05 wt %, 0.10 wt %, and 0.5 wt %) and observed after 24 hours of culture. Wherein, the concentrations of the test groups, 0.01 wt %, 0.05 wt %, 0.1 wt %, and 0.5 wt % are converted to sequentially about 0.03 mg/ml, 0.15 mg/ml, 0.3 mg/ml, and 1.5 mg/ml by the measured absorbance at 280 nm. Microscopic imaging results of the above test groups showed that when the concentration reached 0.5%, the appearance of the cells had no significant change, and also no obvious damage, indicating no adverse effect on the growth of the Hs68 cells. The Hs68 cells were still have a survival rate of more than 90% in each test group by calculation, indicating that the fertilized roe extract had no toxic effects on Hs68 cells.

2. Free Radical Scavenging Test

According to one embodiment of the present invention, DPPH (1,1-diphenyl-2-picrylhydrazyl radical) is used as a reagent to detect anti-oxidant ability, and three repeated tests. As a result, it was found that the fertilized roe extract has a 2.11±0.31 mg/ml of half maximal inhibitory concentration (IC50), which is converted to the concentration of 0.21% by weight that able to eliminate about 50% of free radicals. It is confirmed that the fertilized roe extract has the anti-oxidant ability of eliminating free radicals, thereby assisting the skin against the attack of environmental free radicals and delaying the aging of the skin.

3. Tyrosinase Activity Inhibition Test

According to one embodiment of the present invention, the mouse melanoma cell line (B16-F10; BCRC 60031) was tested and divided into a control group (untreated) and an experimental group. The experimental group was the cells subjected to 0.0125% by weight of the fertilized roe extract and cultured for 72 hours, and then the cells were collected. The cells were lysed by 20 mM Tris-0.1% Triton X-100, centrifuged, and then a portion of the supernatant was used for protein quantitative analysis. The supernatant was added to a solution of L-DOPA (L-3,4-Dihydroxyphenylanine). After reacting at 37° C. for 10 minutes, the absorbance at 475 nm was measured. The results obtained by conversion were as follows: the tyrosinase activity of the control group was taken as 100%, and the tyrosinase activity in the experimental group was only 76.93%. In other words, 0.0125% by weight of the fertilized roe extract had 23.07% inhibition rate of tyrosinase activity. It has been confirmed by the above test that the fertilized roe extract does have an effect of inhibiting the activity of tyrosinase, thereby inhibiting the formation of melanin in the skin and achieving whitening of the skin.

4. Test for Promotion of Collagen Synthesis

Figure 2:
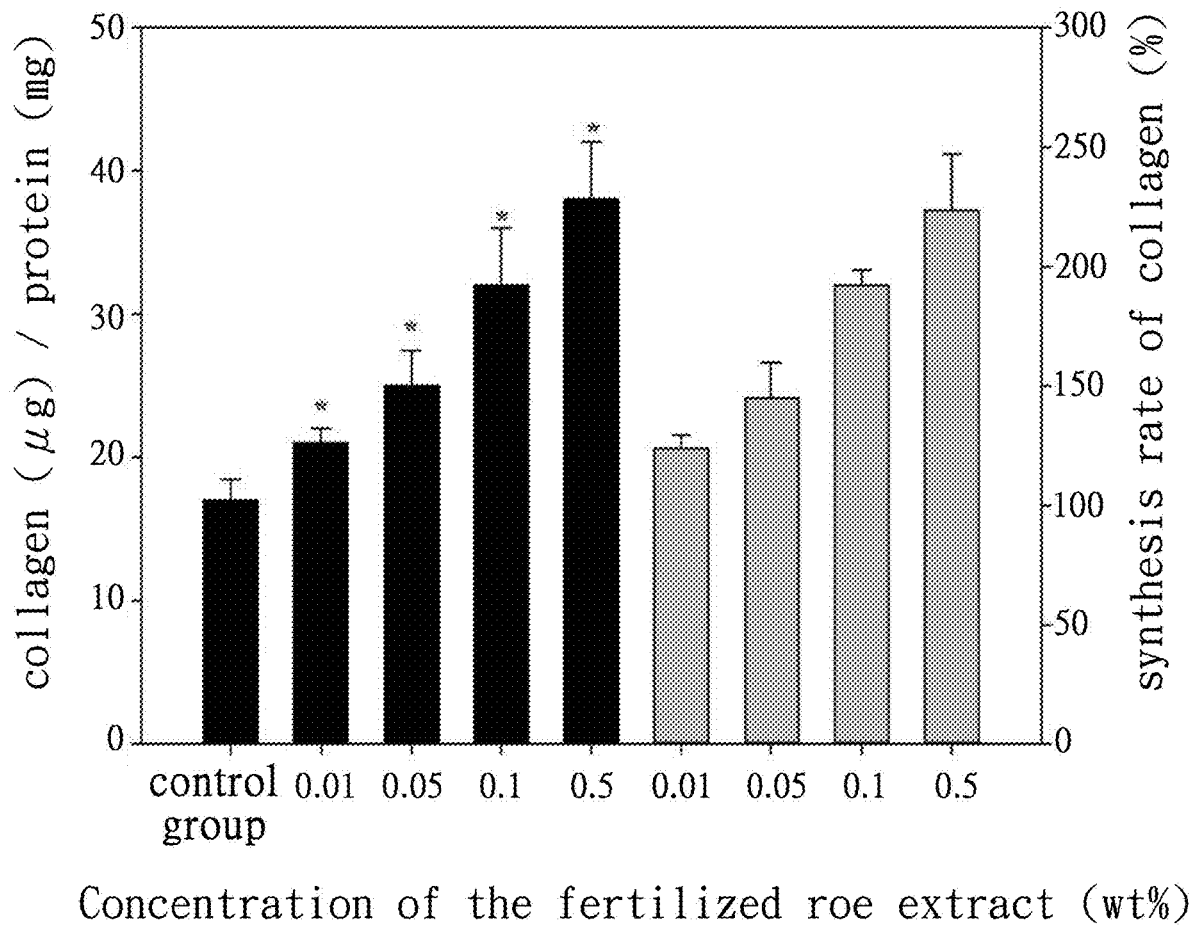
FIG. 2 is a graph showing the effect of promoting collagen synthesis after treatment of human fibroblasts by the fertilized roe extract according to one embodiment of the present invention.

With refer to FIG. 2, it is a graph showing the effect of promoting collagen synthesis after treatment of human fibroblasts cell line (Hs68) by the fertilized roe extract according to one embodiment of the present invention. According to one embodiment of the present invention. The conventional "Total Collagen Assay Kit" (BioVision) was used for detection and analysis. In the experiment, human fibroblasts were used as the test object and added by the fertilized roe extract for culture. The concentration were as follows: control group (0%), 0.01%, 0.05%, 0.1%, and 0.5%, respectively, three repeating tests for each. After 24 hours of culture, the cells were collected, and the cells were lysed with 20 mM Tris-0.1%-Triton X-100, centrifuged, and the protein solution was collected for detection and analysis. The absorbance values of 560 nm of the samples were individually measured. According to the conversion results, compared with the control group, the fertilized roe extracts with the concentrations of 0.01%, 0.05%, 0.1%, and 0.5% were having the collagen synthesis rate of 24%, 48.2%, 88.2%, and 126.4, respectively, and P<0.05 (in the figure*), which means a significant difference from the control group. Although in this embodiment the test groups were tested at the above four concentration points of 0.01%, 0.05%, 0.1%, and 0.5%, etc., and it is reasonably estimated that as the concentration is raised above 0.5%, the collagen synthesis rate is predictably getting better according to the linear relationship of the data result, persons of the skilled art should understand that this concentration range is not limited the effects of promoting collagen synthesis by the embodiment of the present invention. It is known in conventional background knowledge that collagen is the main component of the extracellular matrix of the skin, which keeps the skin elastic, while the loss and aging of collagen causes the skin to lose its elasticity and become wrinkle. Therefore, it can be seen from the above results that promoting the synthesis of collagen in the skin can further achieve the effect of finning the skin, restoring elasticity and smoothing wrinkles, and achieving anti-aging effects on the skin.

5. Test for Promotion of Healing Scalds

The experiment was divided into three groups: the control group (treated with physiological saline for injection), the test group A (the fertilized roe extract as 0.05 wt %) and the test group B (fertilized *Epinephelus coioides* roe extract as 0.05 wt %). The 6 rats were used in each group. A 92° C. copper rod was used to contact on the back skin of each rat for 12 seconds after anesthesia to create a circular deep second-degree scald with about 2 cm in diameter, to establish a scald mode. The scald was re-cleared, medicated and bandaged on the 0th, 1st, 2nd, 3rd, 5th, 7th, 9th, 12th, 15th, 18th, 21st and 24th day after the initiation. The scald was anesthetized with isoflurane on the 0, 1, 2, 3, 5, 7, 9, 12, 15, 18, 21, 24, 28 day and photographed with a camera (scale sticker for correction of the scald). The slides were used to depict the scald and then scanned into a image file, and the wound healing rate (%) was calculated by Image J software. Percentage of wound healing %=[(wound area on day 0−wound area on day N)/wound area on day 0]×100%.

Figure 3:
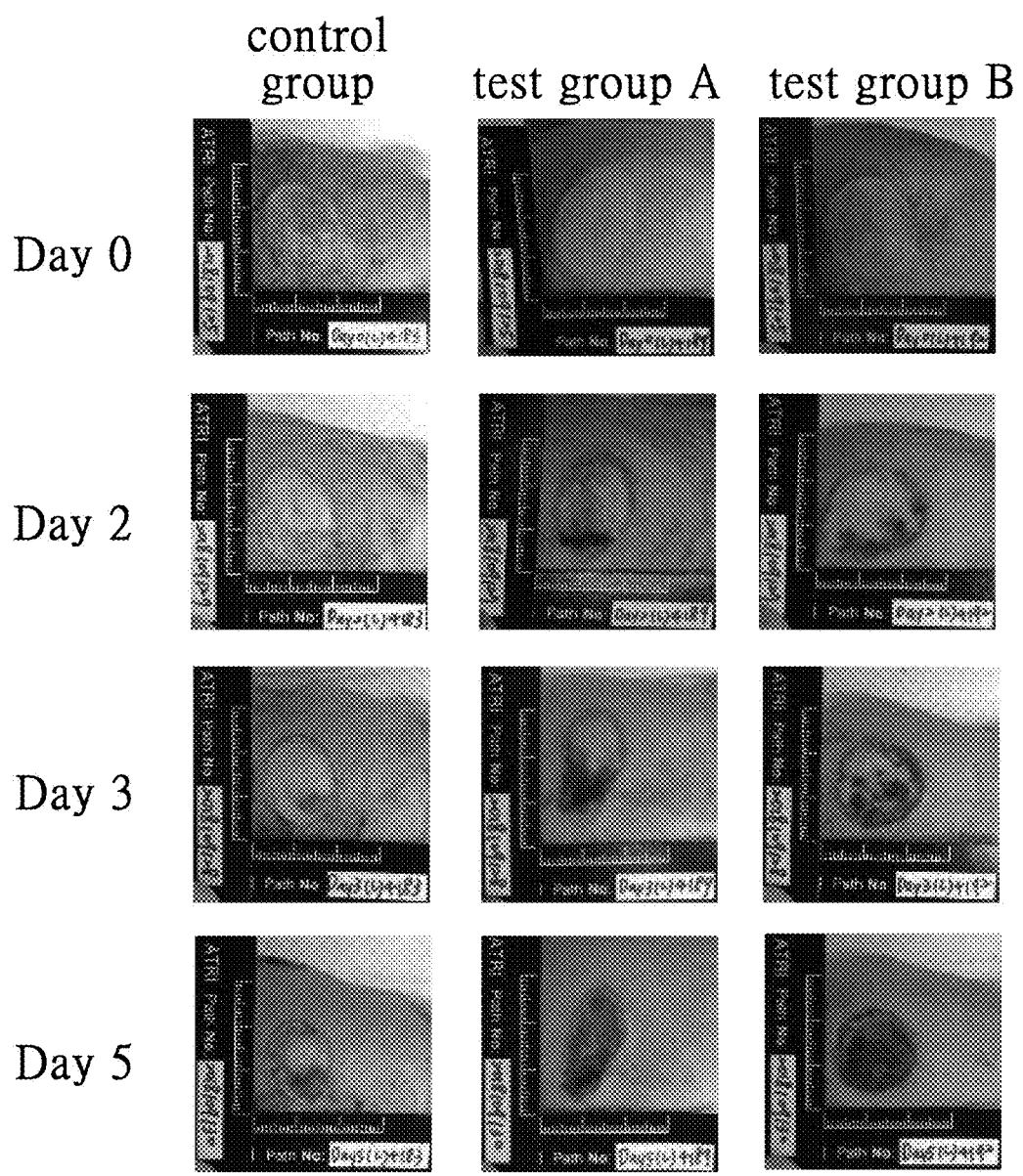
FIG. 3 is an image showing the healing condition after the the treatment of the scald of the rat by the fish fertilized roe extract according to one embodiment of the present invention

With refer to FIG. 3, it is an image showing the healing condition after the the treatment of the scald of the rat by the fish fertilized roe extract according to one embodiment of the present invention. It can be clearly shown that the scalds of the test group A and the test group B was healed and sized decreasingly on day 2 after the initiation, in comparison, the scald of the control group was healing and sized decreasingly on day 5, and thus the healing mechanism of the scald can be started 2 to 3 days earlier. From this, it was confirmed that the fertilized roe extract has an effect of advancing and promoting healing.

Figure 4:
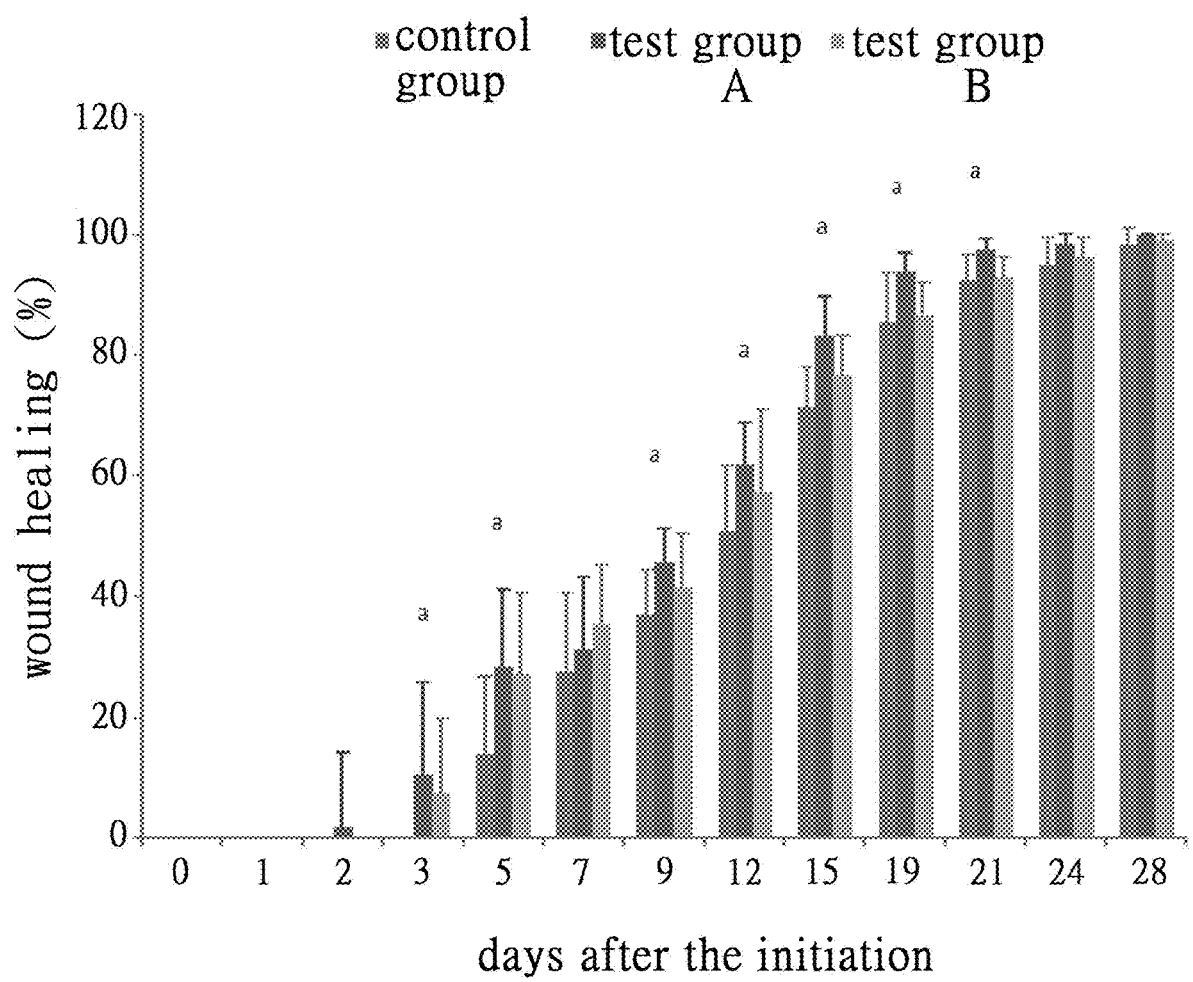
FIG. 4 is a comparison diagram showing the effect of promoting the wound healing after the treatment of the scald of the rat skin by the fertilized roe extract according to one embodiment of the present invention.

With refer to FIG. 4, it is a comparison diagram showing the effect of promoting the wound healing after the treatment of the scald of the rat skin by the fertilized roe extract according to one embodiment of the present invention. It can be clearly shown that the test group A and test group B can indeed advance and accelerate the healing of the scald compared to the control group. It is worth noting that, statistically, the test group A had significant differences on day 3, 5, 9, 12, 15, 19 and 21 (labeled as "a" in the figure) compared with the control group (P<0.05). From this result, we speculate that the fertilized roe extracts from multi-variety mixture may have better efficacy than the fertilized roe extracts from a single variety.

Figure 5:
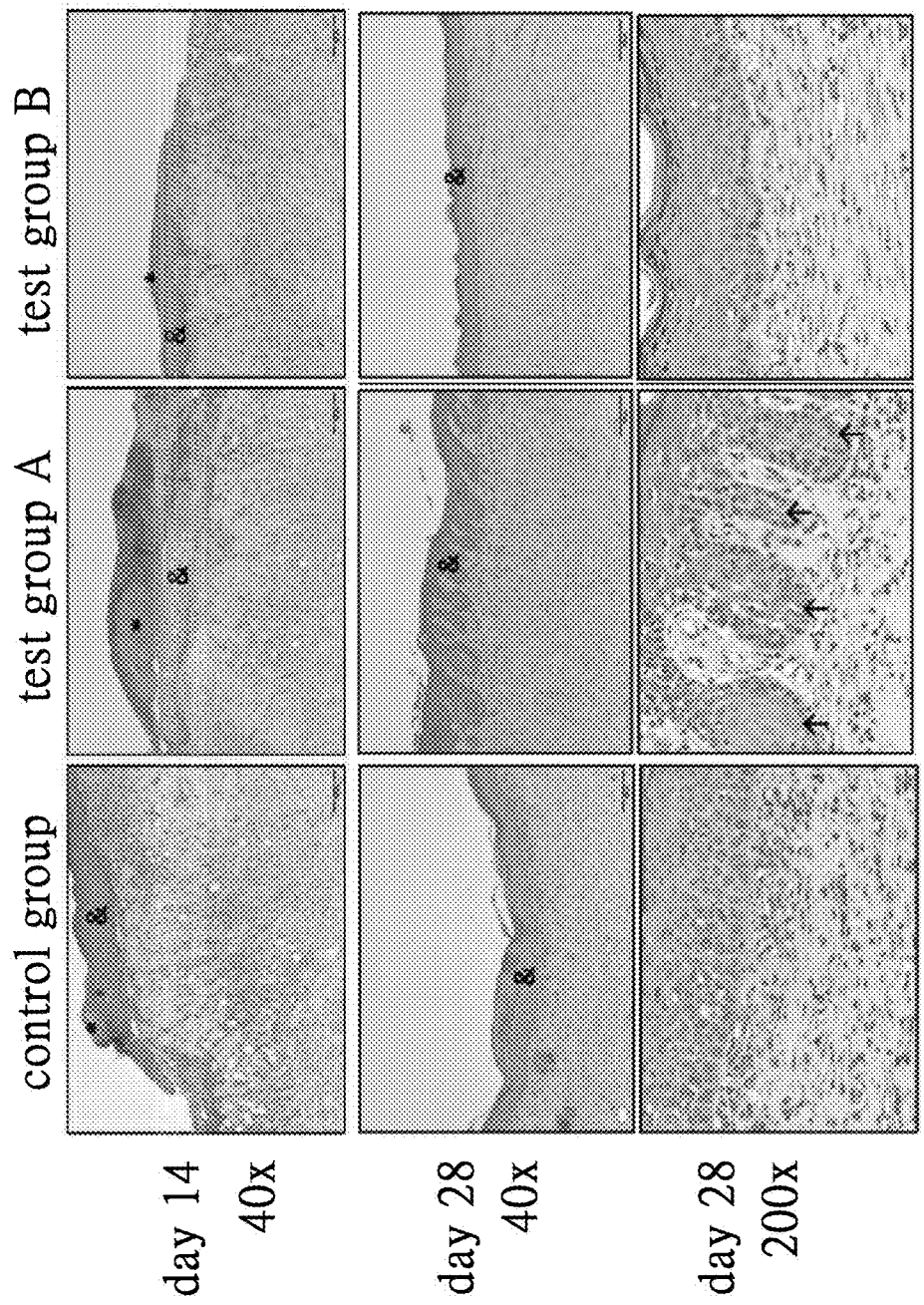
FIG. 5 is a drawing showing the section and staining of the skin tissue of a rat treated by the fertilized roe extract according to one embodiment of the present invention.

With refer to FIG. 5, it is a drawing showing the section and staining of the skin tissue of a rat treated by the fertilized roe extract according to one embodiment of the present invention. The rats in each group were randomly sacrificed to remove the skin of the scald portion on the back on day 14 (proliferation phase), and the remaining rats were sacrificed on day 28 (maturation phase), and the scald portion of the skin on their backs were removed samely. The skins were directly immersed in 10% (v/v) formalin solution for at least 24 hours for tissue sectioning and staining (H&E stain). It is observed under photomicrography (40×, 200×). On day 14, The expressions including the formation of scars (indicated as "*" in the figure), epithelization (indicated as "&" in the figure), polymorphonuclear leucocyte, fibroblast, neovascularization and collagen in each group were no significant differences. On day 28, compared with the control group, the proliferation of fibroblasts in the test group A and the test group B was more significant (p<0.05), indicating that a large amount of collagen were synthesized, and the skin repairs of the epidermis and dermis was promoted (indicated as "&" in the figure). It is worth noting that, compared with the other two groups, the test group A's epithelium tissue grew deeply into deep dermal layer with papillary features like the original structure of dermal papilla (refer to the arrow in the figure). The connecting surface between the epidermis and the dermis is enlarged, which is beneficial to the firm connection of the two, and facilitates the nutrition of the epidermis from the blood vessels of the dermis, so that the remodeling of the structure of the new skin tissue is relatively complete.

According to the above-mentioned test results of the healing of scalds, it is said that this deep second-degree scalds, which damages the epidermal layer and the dermal layer, is a serious skin wound, and it is proved that the embodiments of present invention has the great effects of promoting such severe skin wounds. Therefore, we believe that those of ordinary skill in the art should be able to understand that the fertilized roe extract generally have the same effect of promoting healing of mild skin wounds that only damage the epidermis (such as the minimally invasive surgeries of the medical laser, light scalds, burns, cuts, braises or sunburns).

Combined with the above various test results, it was confirmed that the fertilized roe extract has remarkable effects such as anti-oxidation ability, inhibition of melanin production, promotion of collagen synthesis, and promotion of healing a skin wound, and also has potentials to be applied to phamaceutical products, cosmeceutical products, and dressing materials of medical equipments, thereby creating a new situation in which fisheries and consumers win.

The foregoing embodiments are fully described in the foregoing description of the embodiments of the present invention, and the embodiments of the present invention are merely preferred embodiments of the present invention. The scope of the invention, that is, the equivalent equivalents and modifications of the scope of the invention and the scope of the invention, are within the scope of the invention.

What is claimed is:
1. A method for production of a pharmaceutical composition for skin wounds healing, comprising:
   (a) homogenizing fertilized fish roe in a low temperature aqueous solution at a low temperature ranging between 10° C. and 18° C. by applying ultrasonic waves thereto, thus producing a fertilized fish roe extract homogenate containing protein and peptide molecules of the fertilized fish roe released in said low temperature aqueous solution;
   (b) filtering said fertilized fish roe extract homogenate by subjecting to a multi-stage filtration, thus producing a filtrated fish roe extract; and
   (c) deodorizing the filtrated fish roe extract by applying approximately 1 g of activated carbon per 1 liter of the filtrated fish roe extract, thus resulting in a pharmaceutical composition for skin wounds healing.

2. The method of claim 1, further comprising:
   prior to step (a), obtaining the fertilized fish roe from at least one genus of *Perciformes*.
3. The method of claim 1, further comprising:
   prior to step (a), obtaining the fertilized fish roe from a fish of at least one genus of Epinephelinae subfamily of Serranidae family.
4. The method of claim 1, further comprising:
   prior to step (a), obtaining the fertilized fish roe from a fish selected from a group consisting of *Epinephelus lanceolatus, Epinephelus fuscoguttatus, Epinephelus fuscoguttatus*♀x *Epinephelus lanceolatus*♂, *Epinephelus coioides, Epinephelus malabaricus, Cromileptes altivelis, Plectropomus leopardus, Epinephelus akaara, Epinephelus bruneus, Epinephelus septemfasciatus*, and a combination thereof.
5. The method of claim 1, wherein the pharmaceutical composition is for healing a skin wound selected from a group consisting of an incised injury, a bruise, a burn, a scald, a sunburn, or a combination thereof.
6. The method of claim 1, wherein the fertilized roe extract homogenate has a concentration ranging from 0.01 to 1 wt %.
7. The method of claim 1, further comprising:
   adding at least one pharmaceutically acceptable carrier to said pharmaceutical composition.
8. The method of claim 1, further comprising:
   producing said pharmaceutical composition containing said fertilized roe extract in a form of a liquid, a powder, a granule, a gel, a cream, or a dressing.
9. The method of claim 1, further comprising:
   producing the pharmaceutical composition in an oral or topical dosage form.
10. The method of claim 1, wherein said pharmaceutical composition has therapeutic effects including at least accelerating repair of skin damage, inhibiting tyrosinase activity, and facilitating collagen synthesis.
11. A pharmaceutical composition for prompting the skin wound healing, comprising:
    a fertilized roe extract of a fish, the fertilized roe extract being prepared by:
    (a) obtaining fertilized fish roes from at least *Epinephelus lanceolatus, Epinephelus fuscoguttatus, Epinephelus fuscoguttatus*♀x *Epinephelus lanceolatus*♂, *Epinephelus coioides*, and *Epinephelus malabaricus*, and mixing said fertilized fish roes in substantially equal proportions;
    (b) homogenizing the mixed fertilized fish roes in a low temperature aqueous solution at a low temperature ranging between 10° C. and 18° C. by applying ultrasonic waves thereto, thus producing a fertilized fish roe extract homogenate containing protein and peptide molecules of the fertilized fish roes released in said low temperature aqueous solution, wherein the fertilized fish roe extract homogenate has a concentration ranging from 0.01 to 1 wt %;
    (c) filtering said fertilized fish roe extract homogenate by subjecting to a multi-stage filtration, thus producing a filtrated fish roe extract; and
    (d) deodorizing the filtrated fish roe extract by applying approximately 1 g of activated carbon per 1 liter of the filtrated fish roe extract, thus resulting in a pharmaceutical composition for skin wounds healing.

* * * * *